US00PP17423P2

(12) United States Plant Patent
Briggs

(10) Patent No.: US PP17,423 P2
(45) Date of Patent: Feb. 20, 2007

(54) ***VERONICA* PLANT NAMED 'VERBRIG'**

(50) Latin Name: *Veronica prostrata*
Varietal Denomination: Verbrig

(76) Inventor: Peter Briggs, 1 Crocks Farm Cottages, Bently, Farnham Surrey GU105NH (GB)

( * ) Notice: Subject to any disclaimer, the term of this patent is extended or adjusted under 35 U.S.C. 154(b) by 20 days.

(21) Appl. No.: 11/151,886

(22) Filed: Jun. 14, 2005

(51) Int. Cl.
*A01H 5/00* (2006.01)

(52) U.S. Cl. ..... Plt./251

(58) Field of Classification Search ..... Plt./251
See application file for complete search history.

*Primary Examiner*—Anne Marie Grunberg
*Assistant Examiner*—Annette H Para
(74) *Attorney, Agent, or Firm*—C. A. Whealy

(57) ABSTRACT

A new and distinct cultivar of *Veronica* plant named 'Verbrig', characterized by its upright. outwardly spreading and low mounding plant habit; freely basal branching habit; dense and bushy plant form; variegated foliage; freely flowering habit; and violet blue-colored flowers.

1 Drawing Sheet

Botanical designation: *Veronica prostrata.*
Cultivar denomination: 'Verbrig'.

BACKGROUND OF THE INVENTION

The present Invention relates to a new and distinct cultivar of *Veronica* plant, botanically known as *Veronica prostrata,* and hereinafter referred to by the cultivar name 'Verbrig'.

The new *Veronica* is a naturally-occurring branch mutation of an unnamed selection of *Veronica prostrata,* not patented. The new *Veronica* was discovered and selected by the Inventor in 1996 from within a population of plants of the present selection in a controlled environment in County of Surrey, United Kingdom.

Asexual reproduction of the new cultivar by cuttings since 1996 in County of Surrey, United Kingdom, has shown that the unique features of this new *Veronica* are stable and reproduced true to type in successive generations.

SUMMARY OF THE INVENTION

Plants of the cultivar Verbrig have not been observed under all possible environmental conditions. The phenotype may vary somewhat with variations in environment such as temperature and light intensity without, however, any variance in genotype.

The following traits have been repeatedly observed and are determined to be the unique characteristics of 'Verbrig'. These characteristics in combination distinguish 'Verbrig' as a new and distinct *Veronica* cultivar:

1. Upright, outwardly spreading and low mounding plant habit.
2. Freely basal branching habit, dense and bushy plant form.
3. Variegated foliage.
4. Freely flowering habit.
5. Violet blue-colored flowers.

Plants of the new *Veronica* can be compared to the parent selection. Plants of the new *Veronica* differ primarily from plants of the parent selection in foliage color as plants of the parent selection do not have variegated foliage.

Plants of the new *Veronica* can be compared to plants of the *Veronica* cultivar Blue Sheen, not patented. In side-by-side comparisons conducted in Bressingham, Norfolk, United Kingdom, plants of the new *Veronica* differed from plants of the cultivar Blue Sheen in the following characteristics:

1. Plants of the new *Veronica* were more compact than plants of the cultivar Blue Sheen.
2. During the winter, plants of the new *Veronica* had reddish stems whereas than plants of the cultivar Blue Sheen had green-colored stems.
3. Plants of the new *Veronica* had longer leaves than plants of the cultivar Blue Sheen.
4. Plants of the new *Veronica* had variegated foliage whereas plants of the cultivar Blue Sheen had green-colored foliage.
5. Plants of the new *Veronica* were more freely flowering than plants of the cultivar Blue Sheen.
6. Plants of the new *Veronica* had larger flowers than plants of the cultivar Blue Sheen.
7. Flowers of plants of the new *Veronica* were darker in color than flowers of plants of the cultivar Blue Sheen.

Plants of the new *Veronica* can also be compared to plants of the *Veronica* cultivar Trehane, not patented. In side-by-side comparisons conducted in Bressingham, Norfolk, United Kingdom, plants of the new *Veronica* differed from plants of the cultivar Trehane in the following characteristics:

1. Plants of the new *Veronica* were more compact than plants of the cultivar Trehane.
2. During the winter, plants of the new *Veronica* had reddish stems whereas than plants of the cultivar Trehane had yellow green-colored stems.
3. Plants of the new *Veronica* had broader leaves than plants of the cultivar Trehane.
4. Plants of the new *Veronica* had variegated foliage whereas plants of the cultivar Trehane had yellow green-colored foliage.

5. Plants of the new *Veronica* were more freely flowering than plants of the cultivar Trehane.
6. Plants of the new *Veronica* had larger flowers than plants of the cultivar Trehane.
7. Flowers of plants of the new *Veronica* were darker in color than flowers of plants of the cultivar Trehane.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph at the top of the sheet comprises a side perspective view of a typical flowering plant of 'Verbrig' grown in an outdoor nursery.

The photograph at the middle of the sheet is a close-up view of typical foliage of 'Verbrig' during the summer.

The photograph at the bottom of the sheet is a close-up view of typical foliage of 'Verbrig' during the winter.

DETAILED BOTANICAL DESCRIPTION

Plants shown in the aforementioned photographs and used in the following description were grown under conditions which closely approximate commercial production conditions during the summer and winter an outdoor nursery in the Bressingham, Norfolk, United Kingdom. During the production of the plants, day temperatures ranged from 5 to 28° C. and night temperatures from −8 to 15° C. Plants were about one year old when the photographs and description were taken. In the following description, color references are made to The Royal Horticultural Society Colour Chart, 1995 Edition, except where general terms of ordinary dictionary significance are used.

Botanical classification: *Veronica prostrata* cultivar Verbrig.

Parentage: Naturally-occurring branch mutation of an unnamed selection of *Veronica prostrata,* not patented.

Propagation:

*Type.*—By cuttings.

*Time to produce a rooted young plant.*—About one month during the spring.

*Root description.*—Thick; 159C in color.

*Rooting habit.*—Freely branching.

Plant description:

*Form.*—Perennial. Upright and outwardly spreading plant habit; low mounding. Freely basal branching; dense and bushy plant habit; moderately vigorous growth habit. Numerous flowers arranged on terminal racemes.

*Plant height.*—About 8 to 10 cm.

*Plant witdh.*—About 45 cm.

*Lateral stem description.*—Length (excluding inflorescence): About 15 cm. Diameter: About 1 mm. Internode length: About 5 cm. Aspect: Procumbent. Strength: Moderately strong to strong. Texture: Slightly pubescent. Color, summer: 145A. Color, winter: 145A flushed with 183B.

*Foliage description.*—Arrangment: Opposite, simple. Length: About 3 cm. Width: About 4 mm. Shape: Linear. Apex: Acute. Base: Cuneate. Margin: Entire; slightly undulate. Texture, upper and lower surfaces: Pubescent. Venation pattern: Pinnate. Color: Developing foliage, upper surface: 145A; towards the margins, 1A; in the winter, tinted with close to 183B. Developing foliage, lower surface: 145B; towards the margins, 1B. Fully expanded foliage, upper surface: 145A; towards the margins, 1A; during the winter, tinted with close to 183B. Fully expanded foliage, lower surface: 145B; towards the margins, 1A. Venation, upper and lower surfaces: 144B and 1A.

Flower description:

*Flower arrangement and shape.*—Single saucer-shaped flowers closely spaced on terminal racemes; flowers face mostly outward and upright. Freely flowering habit, about 30 flowers per raceme.

*Natural flowering season.*—Continuous flowering from May to early July in the United Kingdom.

*Flower longevity on the plant.*—Individual flowers last about 15 days on the plant. Flowers not persistent.

*Fragrance.*—Slightly fragrant.

*Flower buds.*—Length: About 4 mm. Diameter: About 2 mm. Shape: Ovate. Color: 96C.

*Inflorescence size.*—Height: About 5 cm. Diameter: About 5 cm.

*Flowers.*—Diameter: About 1 cm. Depth (height): About 8 mm.

*Petals.*—Arrangement: Campanulate; four petals in a single whorl, curved slightly upward and imbricate. Length: About 7 mm. Width: About 5 mm. Shape: Ovate. Apex: Rounded. Margin: Entire. Texture: Smooth, glabrous; satiny. Color: When opening, upper surface: 96C. When opening, lower surface: 96D. Fully opened, upper surface: 92A; color becoming closer to 92C with development; venation, 96C. Fully opened, lower surface: 92B; venation, 96C.

*Sepals.*—Arrangement: Four sepals in a single whorl. Length: About 4 mm. Width: About 1.5 mm. Shape: Lanceolate. Apex: Acute. Base: Cuneate. Margin: Entire. Texture, upper and lower surfaces: Smooth, glabrous. Color, upper and lower surfaces: Close to 145A to 145B; towards the margins, 1A.

*Pedicels.*—Length: About 4 mm. Diameter: About 0.5 mm. Aspect: Mostly erect. Strength: Strong. Color: 145A.

*Reproductive organs.*—Stamens: Quantity per flower: Three. Anther shape: Oblanceolate. Anther length: About 0.3 mm. Anther color: 4D. Pollen amount: None observed. Pistils: Quantity per flower: One. Pistil length: About 4 mm. Stigma shape: Rounded. Stigma color: 4D. Style length: About 4 mm. Style color: 92A. Ovary color: 4D. Seed: Seed development has not been observed.

Disease/pest resistance: Plants of the new *Veronica* have not been noted to be resistant to pathogens and pests common to *Veronica.*

Temperature tolerance: Plants of the new *Veronica* have been observed to tolerate temperatures from −8 to 28° C.

It is claimed:

1. A new and distinct cultivar of *Veronica* plant named 'Verbrig', as illustrated and described.

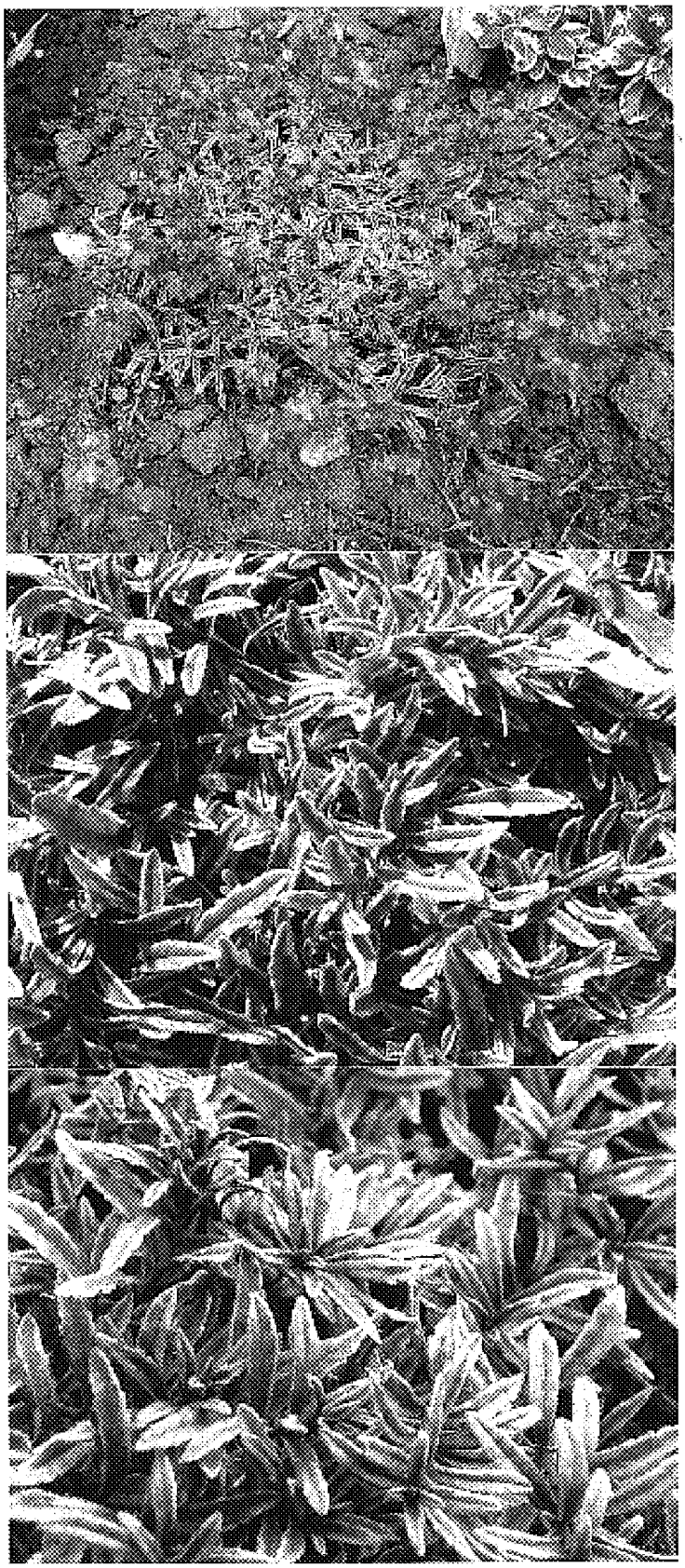

* * * * *